(12) United States Patent
Bakke

(10) Patent No.: US 7,759,273 B2
(45) Date of Patent: Jul. 20, 2010

(54) METHODS OF FORMING AN ALKALI METAL SALT

(75) Inventor: Bart Bakke, The Woodlands, TX (US)

(73) Assignee: Cabot Corporation, Boston, MA (US)

( * ) Notice: Subject to any disclaimer, the term of this patent is extended or adjusted under 35 U.S.C. 154(b) by 1253 days.

(21) Appl. No.: 11/110,268

(22) Filed: Apr. 20, 2005

(65) Prior Publication Data

US 2006/0239900 A1    Oct. 26, 2006

(51) Int. Cl.
*B01J 31/00*     (2006.01)
*B01J 27/053*    (2006.01)
*B01J 27/055*    (2006.01)

(52) U.S. Cl. .............. 502/150; 502/161; 502/170; 502/171; 502/217; 502/218

(58) Field of Classification Search ................ 502/150, 502/161, 170, 171, 217, 218
See application file for complete search history.

(56) References Cited

U.S. PATENT DOCUMENTS

| 3,718,732 | A | 2/1973 | Winslow, Jr. et al. |
| 4,388,291 | A | 6/1983 | Arakawa |
| 6,652,820 | B2 * | 11/2003 | Bakke .................. 423/179 |
| 2004/0045908 | A1 * | 3/2004 | Vuong et al. ............. 210/748 |

FOREIGN PATENT DOCUMENTS

GB     1 504 067     3/1978

OTHER PUBLICATIONS

International Search Report and Written Opinion of the International Searching Authority for PCT/US2006/014081 dated Sep. 29, 2006.

* cited by examiner

*Primary Examiner*—Jerry Lorengo
*Assistant Examiner*—James E McDonough

(57) ABSTRACT

A method of making an alkali metal salt is described and involves (1) reacting at least one alkali metal formate with an least one acid to form an alkali metal salt in the presence of formate ions and (2) substantially removing the formate ions from the alkali metal salt formed in step (1).

31 Claims, 5 Drawing Sheets

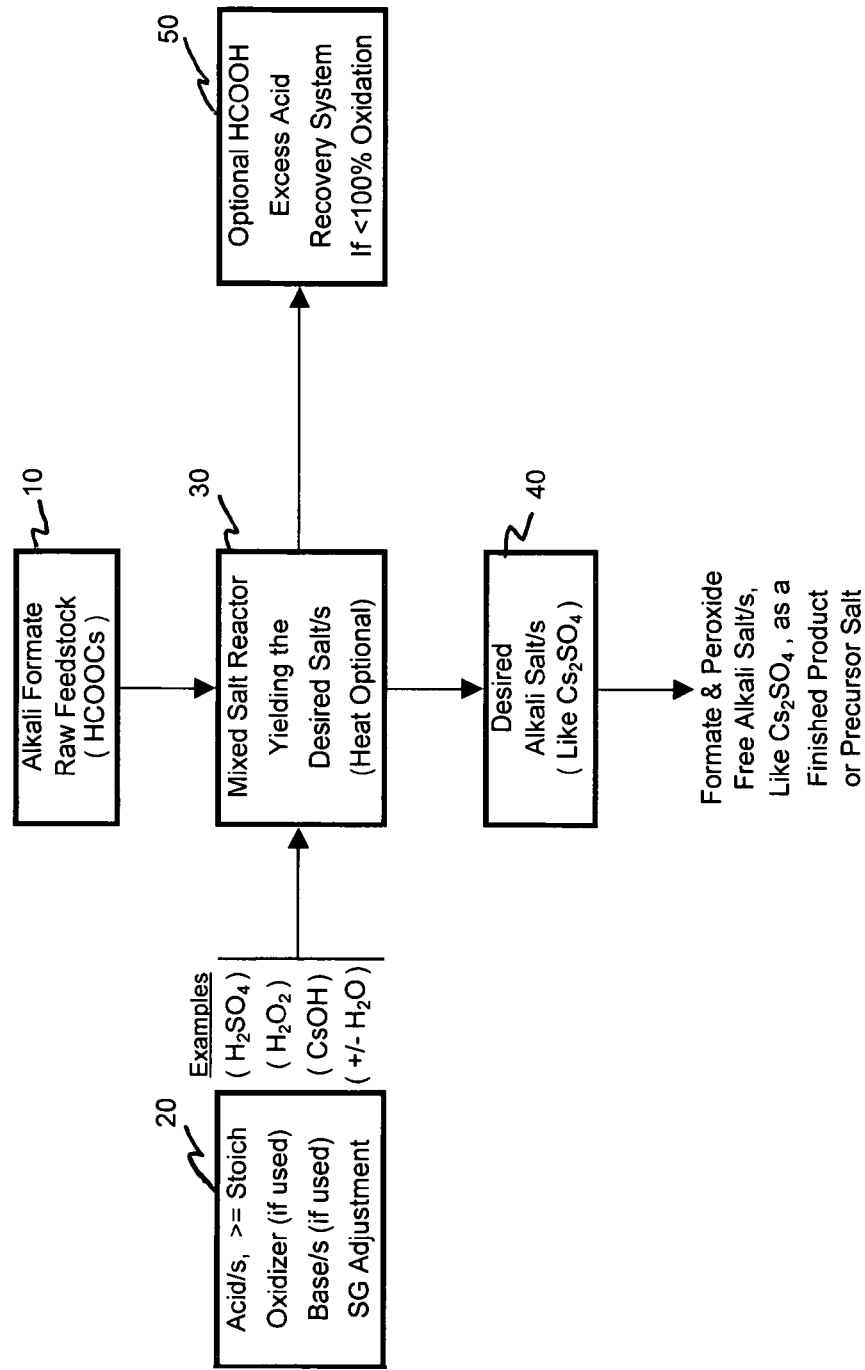
Figure 1 - Complete Conversion from Cesium Formate to Alternative Cesium Salt

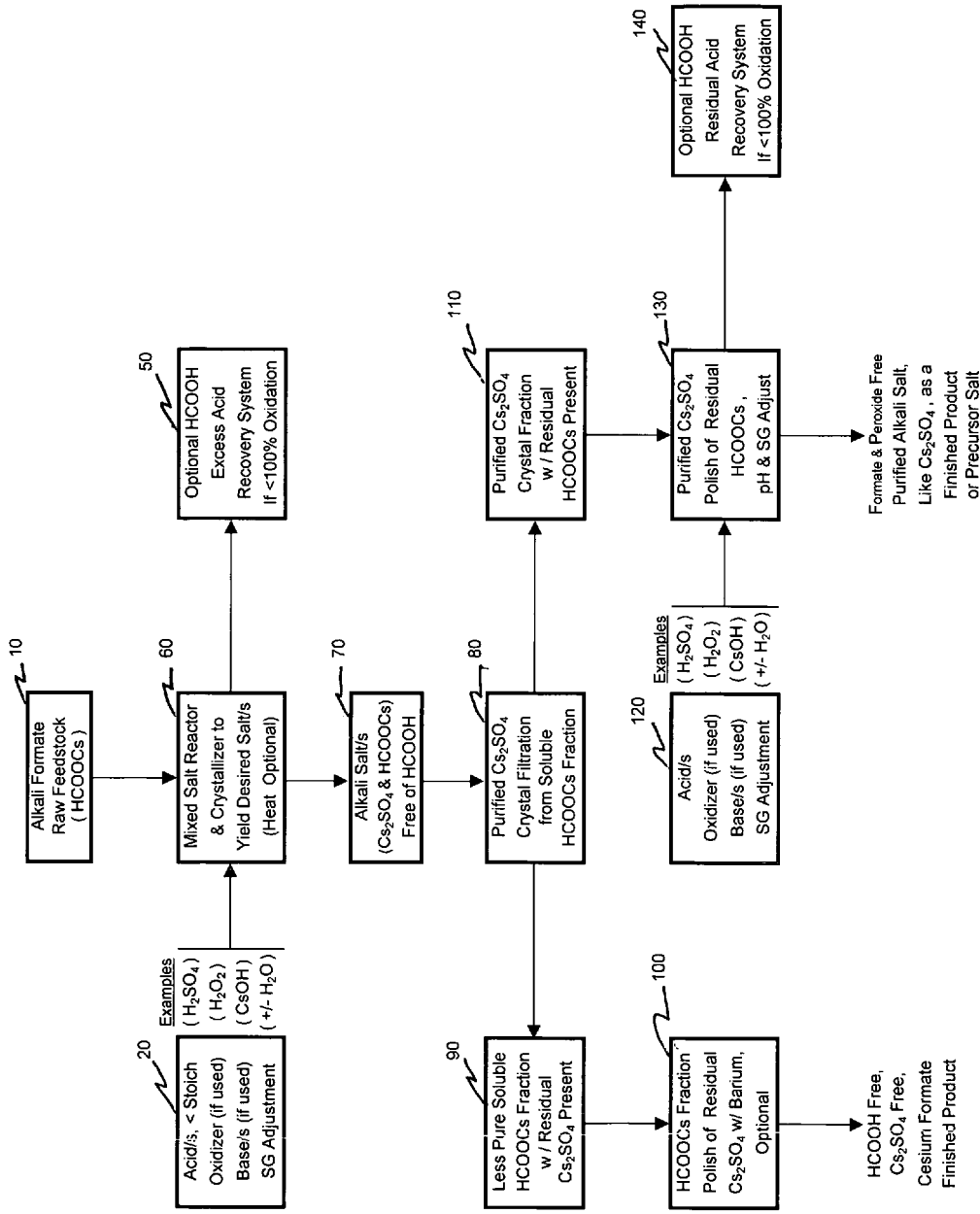
Figure 2 - "One Step" Partial Conversion from Cesium Formate to Alternative Cesium Salt

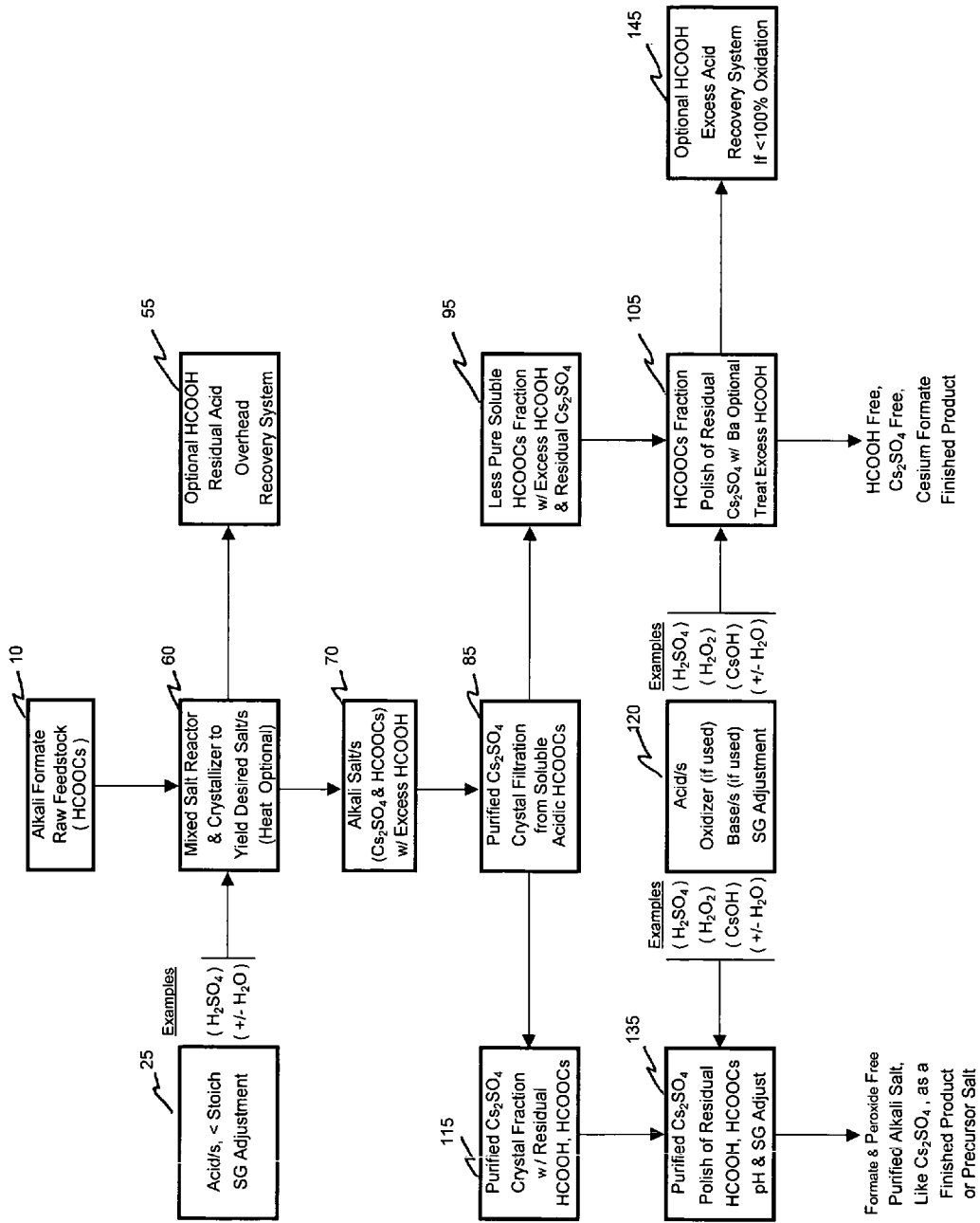
Figure 3 - "Two Step" Partial Conversion from Cesium Formate to Alternative Cesium Salt

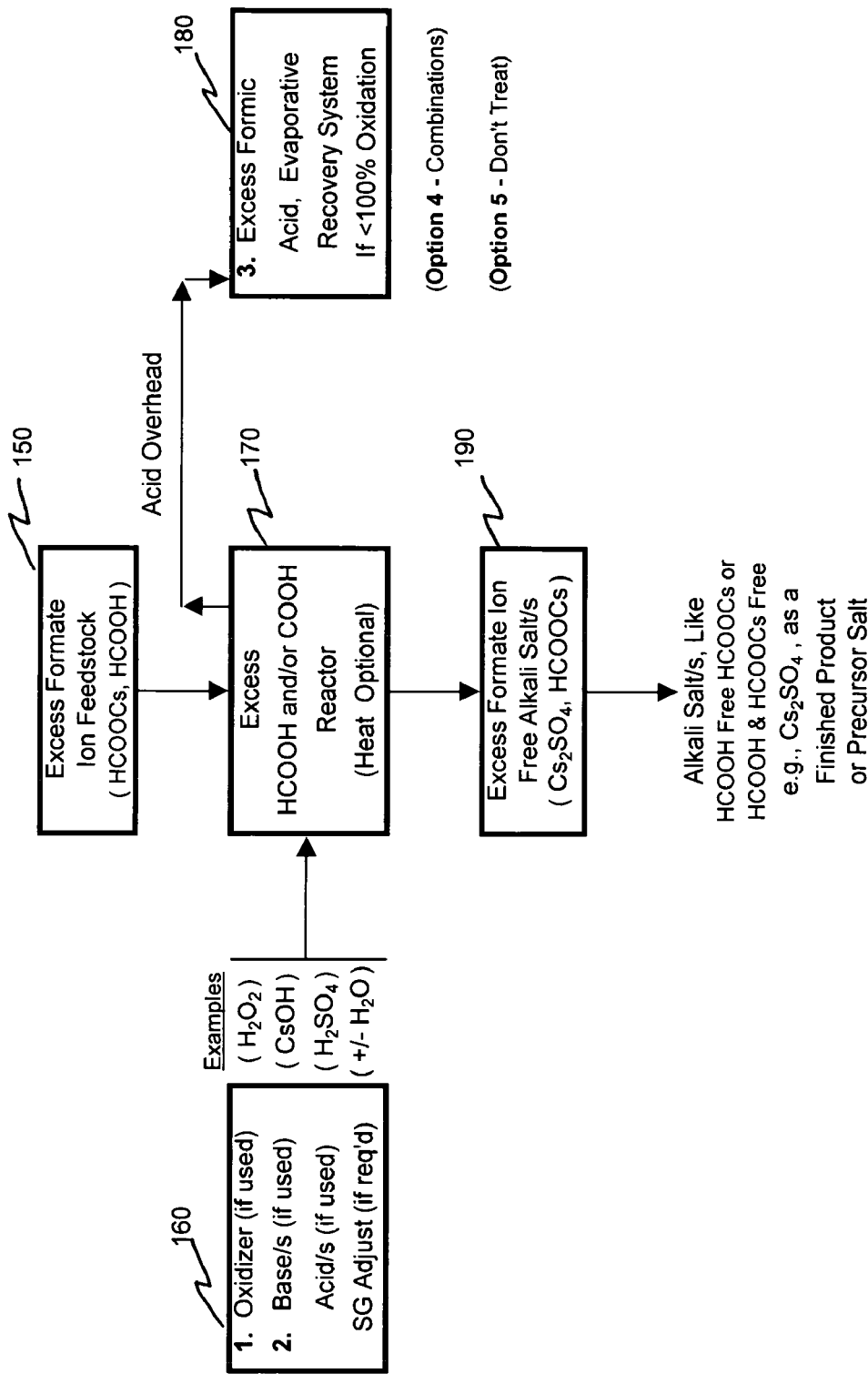
Figure 4 - Three Representations of Treating Excess Formate Ions
NOTE : If treated, alternatives represented can be used in any suitable combinations.

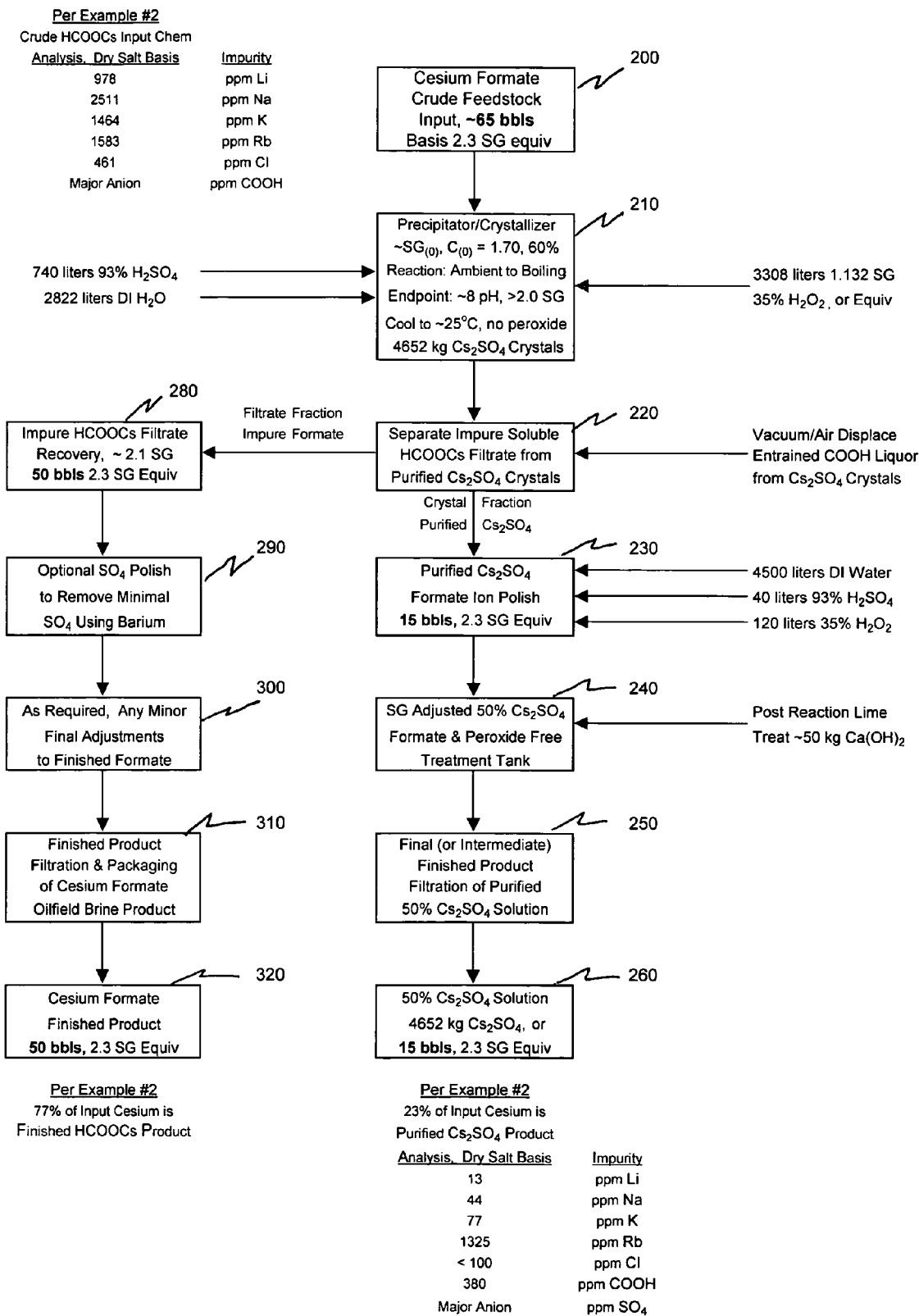

METHODS OF FORMING AN ALKALI METAL SALT

BACKGROUND OF THE INVENTION

The present invention relates to alkali metal salts and methods of making the same.

Alkali metal salts, such as cesium formate, are increasingly being discovered as useful additives for a variety of industrial applications such as in the hydrocarbon recovery areas. The cesium requirements for the oil field applications using cesium formate alone is estimated to be roughly ten times the size of the balance of the cesium salts market and is also projected to continue to grow at a disproportionately faster rate. Given this future market potential of cesium bearing high density alkali formate brines and the possible availability of spent or impure alkali formate blends, it can be envisioned where this salt could serve as a raw material substitute for cesium bearing ores, like Pollucite. Accordingly, there is a desire to develop processes that are capable of producing other alkali metal salts, like cesium salts, including higher purity cesium salts, using an alkali metal formate like cesium formate as a raw material.

Historically, cesium salts have been produced from ore, like Pollucite, using well established methodologies. Some established processing routes have included converting the cesium in the ore to a precursor salt like cesium sulfate, from which other cesium salts are produced. Other methodologies similarly produce alternative cesium salts from precursors like cesium hydroxide and cesium carbonate.

More specifically, barium hydroxide and soluble barium salts have been used as reactants with cesium sulfate solutions in the formation of alkali metal salts. However, barium compounds are very expensive reactants and therefore undesirable.

Other processes have attempted to avoid the use of barium compounds and use cesium aluminum alum which is reacted in the presence of water with calcium hydroxide and a water soluble calcium salt. However, such a process requires the use of a soluble acid salt of lime, like calcium formate, and does not address the removal of many impurities that exist in the alkali metal salt solution that is formed. There is also the risk of having soluble calcium salt contamination in the resultant product if the exact stoichiometric amount required is only slightly exceeded.

Accordingly, there is now a recognized need to develop innovative processes for making alkali metal salts, including purified salts, using cesium formate containing alkali metal formates as the precursor salt versus the more conventional disadvantaged means like those previously described.

SUMMARY OF THE PRESENT INVENTION

A feature of the present invention is to provide a method of making an alkali metal salt which can avoid the time, effort, capital dollars and/or for reagent expense associated with traditional salts produced from ore based raw materials, like cesium bearing Pollucite.

Another feature of the present invention is to provide a method to convert a high density, oil field quality, alkali metal formate solution into a different salt.

An additional feature of the present invention is to provide a process which forms relatively higher purity alkali metal salts without large amounts of impurities.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to methods of forming an alkali metal salt. The method of forming an alkali metal salt includes (a) reacting at least one alkali metal formate with at least one acid to form an alkali metal salt in the presence of formate ions, and (b) substantially removing the formate ions from the alkali metal salt formed in step (a). The method can also include the steps of applying heat and/or adding at least one oxidizer, at least one base or any combinations thereof to the alkali metal salt.

It is to be understood that both the foregoing general description and the following detailed description are exemplary and explanatory only and are intended to provide a further explanation of the present invention, as claimed.

BRIEF DESCRIPTION OF DRAWINGS

FIG. 1 is a flowchart illustrating an exemplary process to completely convert an alkali metal formate, cesium formate, to an alternative cesium salt (or salts) like cesium sulfate.

FIG. 2 is a flowchart illustrating an exemplary one step process to partially convert an alkali metal formate, cesium formate, to an alternative, and purified, cesium salt (or salts) like cesium sulfate, while removing excess formic ions.

FIG. 3 is a flowchart illustrating an exemplary two step process to partially convert an alkali metal formate, cesium formate, to an alternative, and purified, cesium salt (or salts) like cesium sulfate, and to then to subsequently remove the excess formic ions.

FIG. 4 is a flowchart illustrating three distinct ways of treating excess formate ions in accordance with the present invention, while also implicitly allowing for combinations thereof.

FIG. 5 is a scaled flowchart depicting an exemplary illustration of the one-step "Partial Conversion" process complete with one specific set of material balances and processing conditions incorporated. It's intended to illustrate how one very specific version of this process could be deployed on a commercial scale to selectively precipitate, separate, and recover a purified cesium sulfate alternative salt from a crude input cesium formate solution, while returning a suitably restored alkali metal formate oil field brine. Recognizing that there are infinite ways to deploy this technology, using a diversity of raw materials and processing methodologies, this one illustration represents only one narrow set of specific conditions, intended only to facilitate the understanding of the general technology.

DETAILED DESCRIPTION OF THE PRESENT INVENTION

The present invention relates to methods of making alkali metal salts and the products obtained therefrom.

In a preferred method of making the alkali metal salt of the present invention, at least one alkali metal formate is reacted with at least one acid to form at least one alkali metal salt in the presence of formate ions. The formate ions can then be substantially removed from the alkali metal salt formed. For purposes of the present invention, removing the formate ions can involve converting the formate ions to a different chemical form and/or physically removing the formate ions as discussed later.

The reacting of the alkali metal formate with at least one acid can occur at essentially any temperature, and preferably occurs at a temperature of from about 0° C. to about 100° C., more preferably, occurs at a temperature of from about 10° C. to about 50° C.

The alkali metal formate can be reacted with at least one acid by adding at least one alkali metal formate to the reaction. The acid and/or alkali metal formate can be added to the reaction continuously, semi-continuously, as batches, and/or increments. The alkali metal formate of the present invention can be an alkali metal formate solution. The alkali metal formate solution can contain any soluble amount of alkali metal formate in solution (e.g., aqueous solution). For purposes of the present invention, suspended solids can be present in the solution. The alkali metal formate solution can be in the form of a substrate or slurry. From about 1% to about 100% by weight of alkali metal formate is present in the alkali metal formate solution. Preferably, from about 25% to about 90% by weight, and, more preferably, from about 50% to 80% by weight of alkali metal formate is present in the alkali metal formate solution. Preferably, the alkali metal formate is completely dissolved in solution and near or at its saturation density.

The acid used to react with the alkali metal formate can be any type of acid that is capable of reacting with the alkali metal formate to form at least one alkali metal salt. For example, the acid can be sulfuric acid, for instance having a concentration of at least 85 wt %. Other examples include organic acids and inorganic acids like acetic acid, formic acid, propionic acid, butyric acid, nitric acid, halide acids, like hydrochloric, hydrobromic, and hydroiodic acids. In general, carboxylic acids are useful, like unsubstituted carboxylic acids. The amount of acid added in the reaction with the alkali metal formate can be any amount sufficient to obtain the alkali metal salt. A stoichiometric amount is useful or from 10% to 100 wt % of the stoichiometric amount sufficient to convert to the alkali metal salt. As stated above, the acid of the present invention can be added to the reaction continuously, semi-continuously, as batches, and/or increments. The acid can be added in a stoichiometrically deficient amount relative to the at least one alkali metal formate.

The alkali metal salt solution, preferably, has a specific gravity sufficient to precipitate a salt of the at least one acid. In one example, the alkali metal salt solution can be evaporated to have a specific gravity sufficient to precipitate a salt of the at least one acid. Generally, the alkali metal salt solution can have a specific gravity of from about 1.5 s.g. to about 2.4 s.g. More preferably, the specific gravity is from about 1.9 s.g. to about 2.3 s.g.

After forming an alkali metal salt in the presence of formate ions, it is preferable to substantially remove the formate ions from the alkali metal salt. For purposes of the present invention, substantially removing preferably involves removing at least about 50% by weight of the formate ions or at least about 75% by weight of the formate ions, at least about 95% by weight, at least about 99% by weight, or at least about 99.9% by weight of the formate ions. A suitable range would be from about 50% to about 99.95% by weight of the formate ions.

The method for substantially removing the formate ions can include adding at least one oxidizer to the alkali metal salt in the presence of formate ions. The oxidizer used can be hydrogen peroxide or other oxidizers that can achieve the same purpose. Oxidizing can be used to substantially remove the formate ions. Any conventional means to oxidize can be used. The amount of oxidizer added to the alkali metal salt can be an amount sufficient to substantially remove the formate ions from the alkali metal salt. Preferably, the oxidizer is present in a stoichiometric amount of from about 50% to about 300%, and, more preferably, in a stoichiometric amount of from about 75% to about 200%, and, most preferably, in a stoichiometric amount of from about 100% to about 150% relative to the formate ions present. Lower reaction temperatures can be used to conserve energy and to reduce hydrogen peroxide decomposition. Higher temperatures can be used to accelerate the reaction, though the hydrogen peroxide required can increase due to a greater degree of decomposition.

The formate ions can be substantially removed by adding at least one base to the alkali metal salt in the presence of formate ions to convert the formate ions to an alkali metal formate salt. The formate ions can also be substantially removed from the alkali metal salt by filtering. The base used for substantially removing the formate ions can be any type of base. One example of a base is an alkali metal hydroxide, like cesium hydroxide.

The amount of base added to the alkali metal salt can be sufficient to substantially remove the formate ions from the alkali metal salt. Preferably, the base is added in a stoichiometric amount (to react with excess acid) of from about 0% to about 200%, and, more preferably, in an amount of from about 50% to about 150%, and, most preferably, in an amount of about 100% of the stoichiometric amount necessary to consume the excess formic acid.

During the removal of the formate ions (e.g., conversion), the alkali metal salt, or salt solution, can be subjected to heating. The alkali metal salt, or salt solution, can be heated to a temperature and for a time sufficient to assist in substantially removing the formate ions. Preferably, the alkali metal salt in the presence of formate ions is heated to a temperature of from about 40° C. to about 100° C., and for a time of from about 1 hour or more, such as 1 hour to 48 hours or more and more preferably, a temperature of from about 60° C. to about 100° C. Once the desired temperature is reached, the temperature is held for the necessary time to achieve substantial removal of the formate ions.

When heat is utilized, a formic acid vapor overhead can be produced by the heating of the alkali metal salt, or salt solution. When formic acid vapor overhead is produced, the formic acid vapor overhead can be recovered as a formic acid. Conventional methods to recover the vapor and convert it to a liquid or solid can be used.

After removing the formate ions, the alkali metal formate can be neutralized, such as to a pH of 7 or higher. The neutralizing can be achieved by any technique, such as adding a basic material, like, cesium hydroxide or other hydroxide containing materials, like sodium hydroxide, potassium hydroxide, barium hydroxide or the like.

The formic ions (e.g., acidic formate ions) can be substantially removed from the alkali metal salt by one or more of the methods described above. For example, the formic ions can be removed by heating, adding at least one oxidizer, adding at least one base, or any combinations thereof. Separation (e.g., filtration) of a crystalline alkali metal salt fraction from the mixed alkali metal formate salt solution can also be a means of reducing the entrained formate ion present in the recovered crystalline alkali metal salt.

After removing the formate ions from the alkali metal salt, the alkali metal salt can be purified using any conventional purification techniques, including filtration. One advantage of filtering is to separate any gangue material from the alkali metal salt.

At least a portion of the alkali metal salt can be crystallized to obtain crystals. The crystallized alkali metal salt can then be redissolved in an aqueous solution.

The alkali metal salt of the present invention can be any alkali metal salt. For instance, the alkali metal salt can be an alkali metal sulfate. The alkali metal salt (e.g., alkali metal sulfate) can be ultimately converted to, in one or more steps, an alkali metal hydroxide, alkali metal carbonate, alkali metal acetate, alkali metal citrate, alkali metal chloride, alkali metal bromide, alkali metal nitrate, alkali metal iodide, alkali metal propionate, alkali metal oxalate, alkali metal butyrate, alkali metal salicylate, or alkali metal fluoride. An appropriate acid is used to form each of the above alkali metal salts. An exemplary list of acids that can be used include, but are not limited to, acetic acid, citric, hydrochloric, hydrobromic, hydroiodic, nitric, butyric, propionic, oxalic, salicylic, sulfuric, acidic acid, or cesium acetate, or combinations thereof. The acid can be added continuously, semi-continuously, as batches, or increments, or combinations thereof.

The alkali metal salt can be a cesium salt, such as a cesium sulfate. The cesium salt, or at least a fraction thereof, can be converted to cesium hydroxide, cesium acetate, cesium citrate, cesium chloride, cesium bromide, cesium nitrate, cesium iodide, cesium propionate, cesium oxalate, cesium butyrate, cesium salicylate, cesium carbonate, or cesium fluoride. The appropriate acid used for each of the above cesium salts can be an acid such as sulfuric acid, acidic acid, or cesium acetate. Other acids include, but are not limited to, citric, hydrochloric, hydrobromic, hydroiodic, nitric, butyric, propionic, oxalic, and salicylic or combinations thereof.

In the embodiment wherein the alkali metal salt is cesium sulfate, the cesium sulfate, or a fraction thereof, can be converted into cesium hydroxide, cesium carbonate, cesium chloride, or cesium fluoride. The conversion can take place by adding barium hydroxide to the cesium sulfate to produce cesium hydroxide as indicated in the reaction below.

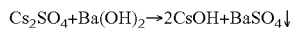

$$Cs_2SO_4 + Ba(OH)_2 \rightarrow 2CsOH + BaSO_4\downarrow$$

Barium sulfate can then be filtered out of the solution. Preferably, the cesium hydroxide is then neutralized with an acid, such as hydrochloric acid, as indicated in the reaction below.

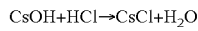

$$CsOH + HCl \rightarrow CsCl + H_2O$$

Processed in this manner, virtually any acid can be substituted for hydrochloric acid in the above equation to yield desired cesium salt. Separately, addition of carbon dioxide to cesium hydroxide yields cesium carbonate and/or cesium bicarbonate.

As depicted in FIGS. 1-4, and further expanded upon in the subsequent discussion of the Figures, the present invention has the ability to convert, as a raw material, an alkali metal formate (further referred to as cesium formate since it is the preferred embodiment) into an alternative alkali metal salt (further referred to as the cesium salt since it is the preferred embodiment). This conversion can be up to 100% where there is effectively little or no purification benefit realized, to partial conversion where purification can occur. Generally, the greater the conversion percentage to the alternative cesium salt, the less will be the purification benefit realized by the alternative cesium salt. The partial conversion process conditions practiced are preferably such that the alternative cesium salt precipitates or crystallizes from the alkali metal formate solution.

The term "Complete Conversion" refers to changing completely a cesium formate salt into an alternative cesium salt. The term "Partial Conversion" also refers to conversion, albeit some portion, of a cesium formate salt into a different cesium salt (and can also involve alkali purification), and can include some non-formate anions, like chloride in cesium sulfate. Again, the partial conversion process conditions practiced are such that the alternative cesium salt preferably precipitates or crystallizes from the alkali metal formate solution.

When referring to the term purification, it is generally intended as impurities present in the cesium formate raw material and not intended as the formate ion itself. The removal of formate ions is generally treated as a separate process. In this context, the general term purification is generally used with respect to the overall (non-formate ion) purity level of the input cesium formate raw material.

For example, when the alternative salt is cesium sulfate, the term purified is primarily in reference to the input alkali and chloride (and like anions) levels of the cesium formate raw material. Aside from the cesium sulfate alternative salt, the term purified is primarily in reference to the input alkali levels of the cesium formate raw material. However, where cesium chloride is the desired alternative salt and if sulfate ion contamination was an issue, then cesium chloride produced by this method would have appreciably reduced sulfate content relative to the input cesium formate.

Another general note on purification, where a purified cesium salt is desired, there is a distinction between crystallization and cold or direct precipitation. The term crystallization, in this context, refers to the application of heat and dissolution of the alternative salt prior to solution cooling and crystal formation. This allows alternative salt crystals to form in an ordered fashion, from the least soluble to more soluble. Generally, this improves the degree of alkali purification of the desired alternative cesium salt. Direct or cold precipitation is less orderly. Here, the alternative acid salt crystals can immediately begin to precipitate upon acid addition. Since the result is less orderly, the degree of alkali purification of the alternative cesium salt can be less than that of the crystallization method, though still frequently quite acceptable.

The degree of purification achieved can be dependent upon various factors. This includes, but is not limited to, the purity level of the input alkali metal formate raw material, the characteristics unique to the alternative cesium salt being produced, including its relative solubility in formate and the salts' fractional re-crystallization properties, the percentage of the alternative cesium salt one wishes to recover from the alkali metal formate feedstock, the temperatures employed, the crystallization and cooling rate temperature profiles, the ending temperature prior to separation, the density of the reacted alkali metal formate solution from which the alternative cesium salt is being recovered, the presence of other salts and types of salts, and the like.

It was previously stated that all process applicable alternative cesium salts realize essentially zero purification benefits (except formate ion removal) when converting 100% of the input cesium formate to the alternative cesium salt. However, there are some non-alkali differences that can result, but for the purposes of this process, they are regarded as favorable ancillary benefits.

While there may be a few exceptions, in general, and if absolute and relative salt solubility's allow, the less one precipitates or crystallizes and recovers, from an alkali metal formate solution, the greater is the degree of purification. Or, alternatively, the greater the conversion percentage to the desired alternative cesium salt, the less is the purification benefit realized by the alternative cesium salt. Again, this assumes that the partial conversion process conditions practiced are such that the alternative cesium salt precipitates or crystallizes from the alkali metal formate solution.

If the objective is the "Complete Conversion" of cesium formate to an alternative cesium salt, then the weight percent of salt solution is unimportant. It can be a dilute or concentrated solution, since there is no precipitating, crystallizing, or separating of an alternative cesium salt crystal from the cesium formate solution.

To produce a purified alternative cesium salt, one can practice a suitable "Partial Conversion" methodology, where the desired intent is to precipitate, crystallize, separate and recover this alternative salt from the input cesium formate solution raw material. Here, the specific solubility of the desired alternative cesium salt in a cesium formation solution can be relevant.

For example, at room temperature, cesium sulfate in a cesium sulfate solution has a saturation density of about 2.0 SG where the concentration is about 64% $Cs_2SO_4$. Beyond this point, cesium sulfate crystals begin to form (e.g., precipitate). This saturation level in a hot solution, as is typical for cesium salts, is far higher. Thus, it is desirable to have a sufficiently cool solution to precipitate the desired crystals. Again, the solubility of cesium sulfate in a cesium formate solution has favorable similarities to that of a cesium sulfate solution; meaning that at cesium formate densities above 2.0 SG, upon sulfuric acid addition, cesium sulfate crystals form, or precipitate, based on ambient conditions. Under these conditions, where the reaction solution density is >2.0 SG, the outcome is virtually quantitative, where all sulfate added as sulfuric acid results in a cesium sulfate salt crystal being precipitated, again based on room temperature conditions (e.g., 25° C.).

If one adds to a >2.0 SG cesium formate solution, an amount of sulfuric acid stoichiometrically consistent with e.g., precipitating 20% of the cesium atoms as cesium sulfate, 20% of the cesium atoms, at room temperature, precipitate as purified cesium sulfate crystals from the cesium form ate solution. The other 80% of the cesium atoms are present generally as soluble cesium formate. This also assumes that the SG of the final solution, post precipitation, is still at or above ~2.0 SG. A solution can be obtained where 20% of the cesium atoms are present as precipitated cesium sulfate crystals, 80% are present as a still soluble cesium formate and the 20% formate ions, formerly associated with the cesium atoms that were subsequently converted to cesium sulfate crystals, are now present as free formic acid.

Unlike cesium sulfate, cesium chloride solubility in cesium formate can be quite different. At room temperature (e.g., 25° C.), cesium chloride, as a cesium chloride solution, has a saturation density of about 1.9 SG where the concentration is about 65% CsCl. Beyond this point, cesium chloride crystals begin to form (e.g., precipitate). This saturation level in a hot solution is again far higher. Hence, there's a need to have a sufficiently cool solution to precipitate the desired crystals. However, unlike cesium sulfate, in a reacted cesium formate solution of 1.90 SG, cesium chloride does not as readily precipitate. To precipitate purified cesium chloride crystals, a higher solution density is generally used.

For example, if one adds to a cesium formate solution an amount of hydrochloric acid stoichiometrically consistent with e.g., precipitating 33% of the cesium atoms as cesium chloride, 27% of the cesium atoms at room temperature precipitate as purified cesium chloride crystals from the cesium formate solution, if this solution is at 2.16 SG. The other 73% of the cesium atoms are present as a mixture of soluble cesium formate and cesium chloride. In this case, a solution can be obtained where 27% of the cesium atoms are present as precipitated and purified cesium chloride crystals, 73% are present as soluble cesium formate and chloride, and their remains a mixture of 27% formate and 5% chloride ions, formerly associated with the cesium atoms that were subsequently converted to cesium chloride crystals, that are now present as free formic acid and hydrochloric acid, respectively. A higher specific gravity solution is required to more quantifiably precipitate an even higher percentage of purified cesium chloride crystals. In this example, at an SG of 2.16, 82% of the chloride ions, added as hydrochloric acid, were precipitated as purified cesium chloride crystals. For cesium chloride, higher solution densities can be used to precipitate percentages greater than the illustrated 82% of theoretical.

Similarly, producing other desired alternative purified cesium salts, by the addition of acid and attention to solution density, can be achieved by adjusting operating conditions based on the behavior of that specific salt in a formate solution. Cesium sulfate can be regarded as a highly desirable alternative cesium salt, as it represents a precursor salt from which other cesium salts can be readily produced.

The following comparative purification data are illustrative only, and are based on varied sample data generated under similar processing conditions. As such, they represent only a portion of all process possibilities. For this purpose, they are intended to depict relative comparisons for a certain set of conditions. Also note that entrained product cross contamination can be impacted by the quality and technique used in the separation of the purified crystals from the less pure cesium formate solution, and, as such, both the absolute degree and the relative degrees of the purification actually achieved can somewhat vary.

Cesium Sulfate Alternative Salt: % Li, Na, K, Rb, Cl Purification (By Weight)
    Complete Conversion—0% Purification
    40-60% Conversion—70, 70, 70, 15, 85
    10-30% Conversion—90, 90, 90, 25, 90

Cesium Chloride Alternative Salt: % Li, Na, K, Rb, $SO_4$ Purification (By Weight)
    Complete Conversion—0% Purification
    40-60% Conversion—90, 90, 90, 80, 90
    10-30% Conversion—90, 90, 90, 80, 90
    General—CsCl is easier to purify than $Cs_2SO_4$, though also more soluble in formate FIG. 1 illustrates an exemplary process to completely convert an alkali metal formate, cesium formate, to an alternative cesium salt (or salts) like cesium sulfate. According to FIG. 1, an alkali formate raw feedstock 10, such as HCOOCs, is introduced into the reactor 30. At least one acid (e.g., $H_2SO_4$), in a stoichiometrically amount, or slight excess, relative to the alkali formate, a specific gravity adjuster (e.g., heat or $H_2O$), and optionally an oxidizer (e.g., $H_2O_2$) and/or a base (e.g., CsOH), are added to the reactor 30. Heat, as required, is applied to the reactor 30. The desired salt, such as $Cs_2SO_4$ is then separated, as required, as indicated at step 40. The $Cs_2SO_4$ can be separated and/or recovered in the form of crystals and/or as a soluble cesium salt solution. Optionally, excess formic acid can be recovered from the reactor 30 by the application of heat and condensed in the recovery system 50 when less than 100% oxidation of the excess formic acid takes place in the reactor 30. In this process, the desired alkali metal salt at step 40 is a formate ion-free alkali metal salt such as $Cs_2SO_4$.

FIG. 2 illustrates a one step partial conversion of an alkali metal formate, cesium formate, to an alternative, and purified, cesium salt (or salts), like cesium sulfate, while removing excess formic ions. In this exemplary embodiment, alkali formate raw feedstock 10 is added to the reactor 60. At least one acid (e.g., $H_2SO_4$) in a stoichiometrically deficient amount relative to the alkali formate, a specific gravity adjuster (e.g., heat or $H_2O$), and optionally, an oxidizer (e.g., $H_2O_2$) and/or a base (e.g., CsOH) as indicated at 20 are also added to the reactor 60. Heat, as required, is applied to the reactor 60. To facilitate the precipitation of the desired alternative cesium salt, like $Cs_2SO_4$, the specific gravity of the alkali (e.g., cesium) metal formate raw feedstock 10 and/or that in reactor 60 should be adjusted, if required, to a sufficiently high enough specific gravity solution to attain good precipitation and recovery of the purified and desired alternative alkali metal salt crystal, like $Cs_2SO_4$. The purified and desired alternative alkali metal salt crystal, like $Cs_2SO_4$, produced in the reactor 60 is then tested at step 70. Optionally, excess formic acid can be recovered from the reactor 60 by the application of heat and condensed in the recovery system 50 when less than 100% oxidation of the excess formic acid takes place in the reactor 60. The alkali metal salts (e.g. $Cs_2SO_4$ and HCOOCs) at step 70 are then separated at step 80, wherein the purified alkali metal salt crystal fraction, such as $Cs_2SO_4$, with residual HCOOCs, are present at step 110, and the less-pure soluble HCOOCs fraction with residual alkali metal salts, such as $Cs_2SO_4$, are present at step 90. The purified alkali metal salt at step 110 is then added to reactor 130 and, if further treatment is desired for formate ion removal, at least one acid (e.g., $H_2SO_4$), a specific gravity adjuster (e.g., heat or $H_2O$), and optionally an oxidizer (e.g., $H_2O_2$) and/or base (e.g., CsOH) at step 120 are also added to the reactor 130. When the reaction in reactor 130 is complete, the alkali metal salt product in the reactor 130 is a formate-free, purified alkali metal salt, such as e.g., $Cs_2SO_4$. Optionally, residual excess formic acid generated in reactor 130 can be recovered from the reactor 130 by the application of heat and condensed in the recovery system 140 when less than 100% oxidation of the excess formic acid takes place in the reactor 130. The sulfate contaminated and less pure soluble HCOOCs at step 90 is reacted with a suitable material, such as e.g., barium formate, at step 100 to produce a cesium formate finished product which is free of HCOOH and sulfates, such as e.g., $Cs_2SO_4$.

FIG. 3 illustrates a two-step partial conversion of an alkali metal formate, cesium formate, to an alternative, and purified, cesium salt (or salts), like cesium sulfate, and then subsequently removes the excess formic ions. In this exemplary embodiment, alkali formate raw feedstock 10 is added to the reactor 60. At least one acid 25 (e.g., $H_2SO_4$) in a stoichiometrically deficient amount relative to the alkali metal formate and a specific gravity adjuster (e.g., heat or $H_2O$) are added to the reactor 60. Heat, as required, is applied to the reactor 60. To facilitate the precipitation of the desired alternative cesium salt, like $Cs_2SO_4$, the specific gravity of the alkali (e.g., cesium) metal formate raw feedstock 10 and/or that in reactor 60 should be adjusted, if required, to a sufficiently high enough specific gravity solution to attain good precipitation and recovery of the purified and desired alternative alkali metal salt crystal, like $Cs_2SO_4$. The purified and desired alternative alkali metal salt crystal produced in the reactor 60 is then tested at step 70. Optionally, some portion of the excess formic acid can be recovered from reactor 60 by the application of heat and condensed in the recovery system 55. The alkali metal salt recovered in Step 70 includes the alkali metal salt, such as $Cs_2SO_4$, HCOOCs and excess HCOOH. In the overhead recovery system 55, the residual acid is optionally recovered. At step 85, the alkali metal salts are then separated, by filtration of the purified alkali metal salt crystal, such as $Cs_2SO_4$, from the less pure alkali metal (e.g., cesium) formate solution. The less pure soluble HCOOCs fraction containing the majority of the excess HCOOH and with slight sulfate contamination from residual alkali metal salt (e.g., $Cs_2SO_4$) are recovered as indicated at step 95 and, as required, are then added with ingredients in step 120, which can include at least one acid (e.g., $H_2SO_4$), specific gravity adjuster (e.g., heat or $H_2O$), and optionally, an oxidizer (e.g., $H_2O_2$) and/or a base (e.g., CsOH), as indicated at step 105. Reactor 105, post-reaction product, is a sulfate contaminated and less pure soluble HCOOCs fraction. This solution is then reacted with a suitable material, such as e.g., barium formate, at step 105 to produce an alkali metal formate product, such as a cesium formate finished product, which is free of HCOOH and sulfates, such as e.g., $Cs_2SO_4$. Optionally, excess formic acid can be recovered from the reactor 105 by the application of heat and condensed in the recovery system 145 when less than 100% oxidation of the excess formic acid takes place in the reactor 105. The purified alkali metal salt (e.g., $Cs_2SO_4$) crystal fraction with residual HCOOH and HCOOCs at step 115, as required, are then added with ingredients in step 120, which can include at least one acid (e.g., $H_2SO_4$), a specific gravity adjuster (e.g., heat or $H_2O$), and optionally, an oxidizer (e.g., $H_2O_2$) and/or a base (e.g., CsOH) as indicated at step 135 to obtain purified alkali metal salt (e.g., $Cs_2SO_4$), with residual HCOOH and HCOOCs having now been removed. The pH and the specific gravity are then adjusted in the reactor 135 to obtain formate free, purified alkali metal salt, such as $Cs_2SO_4$ as the finished product or precursor salt.

FIG. 4 illustrates three distinct representations of treating excess formate ions, while also implicitly allowing for combinations thereof. According to FIG. 4, excess formate ion feedstock, such as HCOOCs and HCOOH at 150, are added to the reactor 170. Optionally, at least one acid (e.g., $H_2SO_4$), a specific gravity adjuster (e.g., heat or $H_2O$), and optionally an oxidizer (e.g., $H_2O_2$) and/or a base (e.g., CsOH), at step 160, are added to the reactor 170. Heat, as required, is applied to the reactor 170. Optionally, excess formic acid can be recovered from the reactor 170 by the application of heat and condensed in the recovery system 180 when less than 100% oxidation of the excess formic acid takes place in the reactor 170. If treated for formate ion, the alkali metal salt/s product of the reactor 170, as represented by step 190, can be produced free of excess formate ion contamination.

The present invention will be further clarified by the following examples, which are intended to be purely exemplary of the present invention.

EXAMPLES

The examples below illustrate some process alternatives as depicted in the figures and as discussed above. These are intended only as illustrations of how the technology can be deployed and by no means is it intended to narrow the scope of the possible breadth of processing alternatives.

Pursuant to alternative processing methodologies outlined, the formate raw material is converted into a different cesium salt, if desired, and into a more purified form of a cesium salt, if desired, through the addition of at least one acid and by the removal or treatment of the input formate ion. The input formate raw material is partially or totally converted into an alternative acid salt and can be purified by varied crystallization techniques. The desired alternative cesium salt product can then be deployed into other suitably applicable cesium salt applications.

Under specific conditions, hydrogen peroxide can be used successfully to oxidize the formate anion in various solutions yielding carbon dioxide and water. In the presence of an acid, cesium formate can be oxidized and converted into a different cesium salt solution. For example, and in the appropriate ratios, additions of sulfuric acid and hydrogen peroxide to a cesium formate solution can produce a cesium sulfate solution, free of formate ion. This conversion process can be partial or complete. Similarly, other acid salts of cesium can be extracted or produced from a cesium formate salt solution. Furthermore, desired alternative cesium salts can be extracted, separated, recovered and purified, as desired, for commercial non-oilfield applications. These techniques provide a means to produce alternative cesium salts, including purified cesium salts, from a non-traditional and quite unique cesium containing raw material. Ultimately, any cesium salt can be successfully produced using a crude cesium formate salt as a raw material.

High Density Formate Raw Material:

A high-density cesium formate oil field brine solution was used as the raw material for the examples. A formate feedstock solution of ~81.5% cesium formate was acquired for use as the raw material for the examples depicted below. The sample was analyzed for the targeted impurities to assess changes and improvements. Relevant analyses of this input formate raw material are provided below and are reported on a dry cesium formate basis. Alkalis were measured by Atomic Absorption. Anions were measured by Ion Chromatograph.

Lithium 978 ppm
Sodium 2511 ppm
Potassium 1464 ppm
Rubidium 1583 ppm
Sulfate<12 ppm
Chloride 461 ppm
Formate Major Component (MC)

Example #1

Representative of FIG. 1

Example 1 depicts the complete conversion process where an input cesium formate salt solution raw material is in effect completely converted into an alternative cesium salt. Sulfuric acid is used as a raw material to produce the alternative cesium salt for the $Cs_2SO_4$ acid salt. Hydrogen peroxide is used to oxidize the formate ion allowing the near complete conversion from cesium formate to cesium sulfate. The cesium sulfate salt is then further processed to produce, recover and separate a purified cesium sulfate salt fraction from a less pure cesium sulfate salt fraction.

Added to a one liter sample of cesium formate feedstock solution was 1250 g of 50% sulfuric acid solution. The addition was done slowly and began at room temperature to minimize the solution temperature increase. The addition of acid was in slight excess (10-15%) to that required to ultimately convert all of the cesium formate to cesium sulfate. The excess acid has the added benefit of creating an acidic environment in which oxidation of the formate ion is more favorable. Incremental additions of 35% hydrogen peroxide were added to the mixed acid salt solution to control the temperature and reactivity of the mix. The additions were made to control the temperature to less than 60° C. A total of 1250 ml, or 28% excess, was added to the mix over a period of seven hours. Evidence of the reaction was seen clearly by the robust liberation of $CO_2$. Cooling capability of the solution would have allowed bulk additions to be made, as temperature and therefore reactivity would have been controllable. The solution was allowed to agitate overnight at room temperature.

The next day the solution was heated to 50-60° C. for 8 hours under agitation. The selected temperature range was chosen to accelerate the reaction using heat, but to lessen the thermal decomposition of hydrogen peroxide associated with high temperatures. Throughout the 8 hours, there was appreciable liberation of $CO_2$, though clearly lessening in intensity with time. The solution was then allowed to cool and again agitate overnight. A sample was taken the next morning and submitted for ppm of formate ion. The result on a dry salt basis was 66000 ppm. This result indicated that about 75% of the input formate ion had been successfully oxidized and converted to cesium sulfate.

The heating process began again after the above sample was taken. The reaction was allowed to proceed again under agitation for a period of 7 hours, controlling the temperature to within 50-60° C. The liberation of $CO_2$ again diminished with time. The solution was allowed to cool to room temperature and agitate overnight.

The next day the reaction solution was again heated-up to 50-60° C. under agitation. The effervescing associated with $CO_2$ liberation was quite muted, suggesting the reaction was at least nearing completion. It was decided to add 1250 ml of distilled water and boil down the reaction solution to advance any remaining reaction and to enhance the decomposition of some of the excess hydrogen peroxide. Six hours at boiling were allowed before allowing the reaction solution to cool and agitate overnight.

The process was effectively repeated the following day, however allowing the solution to cool and agitate over the weekend. Having felt that reaction was complete, the reaction solution was neutralized with hydrated lime to an elevated pH of 11.4 to facilitate hydrogen decomposition. Elevated pH's and temperatures improve this decomposition rate. There was appreciable effervescing upon lime addition, suggesting residual excess hydrogen peroxide decomposition. The slurry was then filtered to separate the gangue material, comprising mainly calcium sulfate, from the cesium sulfate filtrate.

The cesium sulfate filtrate was then boiled down in level to an estimated volume consistent with about 50-60 percent of the starting cesium sulfate salt to crystallize out on a room temperature basis. When the volume was achieved, the agitated solution was allowed to cool to 30-35° C. This solution was then vacuum filtered to separate the purer crystallized cesium sulfate salt from the saturated less pure cesium sulfate mother liquor filtrate. The approximate final split was roughly calculated to be ~59% of the cesium sulfate recovered as purified crystals and the ~41% balance remained as soluble cesium sulfate reporting in the crystal filtrate mother liquor. The purified crystals were then re-dissolved using pure water to a salt concentration of ~51%. The less pure saturated cesium sulfate mother liquor was adjusted downward in density to a concentration of ~52% by the addition of pure water.

Both solutions were then submitted for analysis. The results reported below are on a dry cesium sulfate basis. To the left for comparison, is the input cesium formate results recalculated on an equivalent dry cesium sulfate basis (except for input ppm formate and sulfate ion). Alkali analyses were conducted by Atomic Absorption. The anion analyses were conducted by Ion Chromatograph.

|  | Input<br>Stock Solution | Purified<br>$Cs_2SO_4$ Fraction | | Less Pure<br>$Cs_2SO_4$ Fraction | |
|---|---|---|---|---|---|
| Lithium | 962 ppm | Lithium | 451 ppm | Lithium | 1561 ppm |
| Sodium | 2469 ppm | Sodium | 275 ppm | Sodium | 4064 ppm |
| Potassium | 1440 ppm | Potassium | 315 ppm | Potassium | 2530 ppm |
| Rubidium | 1557 ppm | Rubidium | 1108 ppm | Rubidium | 1821 ppm |
| Sulfate | <12 ppm | Sulfate | Major Peak | Sulfate | Major Peak |
| Chloride | 454 ppm | Chloride | 79 ppm | Chloride | 1103 ppm |
| Formate | Major Peak | Formate | 22 ppm | Formate | 68 ppm |

It's clearly illustrated that the formate ion was near completely eliminated. The purification effect is also quite evident. However, the lithium purification result was less than expected. This was believed to have been attributable to a pH over adjustment using lime just prior to the crystallizing boil down step. This was done to both decompose excess peroxide and to neutralize the modest excess of sulfuric acid added at the initial reaction step to facilitate formate ion oxidation. It is surmised that upon the crystallizing boil down step that carbonate presence facilitated the precipitation of an insoluble lithium in the form of a carbonate and was precipitated with the crystallized purified cesium sulfate salt during the crystallizing boil down step.

The trial was repeated using the same cesium formate feedstock paying careful attention to managing conditions that could contribute to this possibility. As illustrated below, the lithium purification was much improved. The ppm lithium in the purified cesium sulfate fraction was reduced to 121 ppm on a dry salt basis. The complete alkali analysis reported for the purified cesium sulfate fraction is depicted below. Only the reported lithium is appreciably different than previous.

| Purified $Cs_2SO_4$ Fraction | |
|---|---|
| Lithium | 121 ppm |
| Sodium | 278 ppm |
| Potassium | 341 ppm |
| Rubidium | 1084 ppm |

Example #2

Representative of FIGS. 2 & 5

Example 2 illustrates the "One Step" partial conversion process where an input cesium formate salt solution raw material is converted into both a formate ion entrained crystallized and purified cesium sulfate product and an impure, excess formate ion free, cesium formate mother liquor. Further polishing of the purified product fraction was pursued to appreciably reduce the residual entrained formate ion.

Analyses are provided in appropriate sections below. Where primary salt product applicable, references to primary salt component anions like formate, sulfate and/or chloride are reported only as a major or the primary component as detected by Ion Chromatographic analysis (i.e., as applicable, the major or primary anion peak detected).

Added to a 500 ml sample of cesium formate feedstock solution was pure water to a beaker volume of ~680 ml, 204 ml 35% hydrogen peroxide solution and 83 ml 50% sulfuric acid. This starting solution was boiled down and ambient cooled to a targeted 450-500 ml beaker volume of solution to allow near complete crystallization and precipitation of cesium sulfate crystals from the starting cesium formate solution and tested. The specific gravity of the aqueous component of the solution was about 1.98. Test strips to detect the presence of peroxide were negative. The solution pH was about 6.06 at 25° C. indicating that excess formic acid still remained. The solution pH and the lack of peroxide presence suggested that the hydrogen peroxide added had decomposed from the aggressive heating step before the desired reaction was complete.

Added to this incompletely reacted solution was pure water to a level of 900 ml and another 204 ml of hydrogen peroxide. After sitting overnight at room temperature, the boil down process was repeated. To avoid a vigorous reaction with the excess hydrogen peroxide now present, the solution was brought up in temperature until it was clear that the reaction solution could be boiled down to a similar final beaker volume target, though closer to ~450 ml to achieve >2.0 SG. When this approximate volume target was achieved, the agitated solution was allowed to cool to room temperature allowing for the near complete crystallization and precipitation of the purified cesium sulfate crystals from the starting cesium formate solution. The solution was then tested. The desired target of pH neutrality, an absence of excess peroxide and an aqueous specific gravity of >2.0 were all successfully achieved. It is noted, that in contrast to Example #3 below, no formic acid fumes were apparent or detected while the preceding thermal processing steps were being conducted.

The purified cesium sulfate crystals were then separated from the impure aqueous cesium formate mother liquor solution by vacuum filtration. Only vacuum drying was applied. The recovered cesium sulfate crystals were then added to pure water and yielded a 52% cesium sulfate solution. Both the recovered impure cesium formate filtrate and the purified 52% cesium sulfate solution were submitted for chemical analysis. The cesium atoms recovered as cesium formate and those recovered as cesium sulfate were calculated. Consistent with the theoretical expectations of the quantity of sulfuric acid added, ~23% of the cesium atoms were recovered as cesium sulfate crystals and ~77% of the cesium atoms were recovered as soluble cesium formate salt. Chemical analyses reported on a dry salt basis for both fractions are provided below. Where applicable, the formate and sulfate content are reported only as a major or the primary component from the Ion Chromatographic analysis (i.e., the major or primary anion peak detected).

| Impure<br>Cs Formate | | Purified<br>$Cs_2SO_4$ | |
|---|---|---|---|
| Lithium | 1266 ppm | Lithium | 13 ppm |
| Sodium | 2640 ppm | Sodium | 44 ppm |
| Potassium | 1740 ppm | Potassium | 77 ppm |
| Rubidium | 1726 ppm | Rubidium | 1325 ppm |
| Sulfate | 2406 ppm | Sulfate | Major |
| Chloride | 553 ppm | Chloride | <100 ppm |
| Formate | Major | Formate | 8800 ppm |

No further treatment of the impure cesium formate solution was pursued to remove the very minimal amount of sulfate that was entrained as a cross-contaminant during the vacuum filtration separation of the purified cesium sulfate crystals from the impure soluble cesium formate solution. Traditional well-established sulfate removal techniques, known to those in the art, like barium compound additions, can be pursued, if further sulfate reductions are desired.

Further treatment of the purified cesium sulfate fraction was pursued to reduce the minimal amount of formate ion that was entrained as a cross-contaminant during the vacuum filtration separation of the purified cesium sulfate crystals From the impure soluble cesium formate solution.

Added to 135 ml of ~1.70 SG purified cesium sulfate solution was 6 ml of 35% hydrogen peroxide, 6 ml of ~97.5% sulfuric acid and 250 ml of pure water. This solution was then reacted and maintained at a temperature range of ~55-85° C. to an adjusted final volume consistent with a projected final specific gravity of ~1.7 SG. When completed, the solution tested as modestly positive for the presence of peroxide. The cesium sulfate reaction solution was deemed sufficiently close enough to have achieved at least near completion for the removal of the formate ion contaminant.

To avoid, minimize or reduce potential anion peaks interference, prior to conducting an Ion Chromatograph analysis for formate, sulfate and chloride content, the reacted cesium sulfate solution was then further treated, converting it to a cesium hydroxide solution by treatment with barium hydroxide. It should be noted that the type of hydrogen peroxide used throughout these trials was purposefully selected due to its pH and temperature decomposition sensitivity. As such, any excess was expected to fully decompose when the modestly peroxide bearing cesium sulfate solution was converted to a cesium hydroxide solution, per the processing conditions as illustrated below.

Added to 140 ml of ~1.7 SG cesium sulfate solution was 200 ml of pure water. The water was added to thin the solution modestly for barium treatment. This solution was heated to ~65° C. and then reacted with 68 grams of barium hydroxide monohydrate. While maintaining a solution temperature of ~65-75° C., the reaction was allowed to proceed for ~30 minutes. This reaction solution was then filtered to separate the principally barium sulfate gangue from the aqueous cesium hydroxide solution product. The vacuum filtered barium sulfate gangue was washed in situ with 104 ml of pure water to displace gangue entrained cesium hydroxide solution product. The recovered, diluted ~18% cesium hydroxide solution was then tested for peroxide presence. As expected, the basic solution tested negatively for the presence of any residual peroxide, indicating that the excess peroxide, previously present in the purified cesium sulfate fraction, had successfully decomposed when subjected to the modest heat and elevated pH processing conditions.

Prior to anion analysis by Ion Chromatograph, the diluted aqueous cesium hydroxide solution was first densified through evaporation to achieve a ~50% cesium hydroxide solution. A sample was then analyzed for formate, sulfate and chloride anion content by an Ion Chromatograph. Aside the input cesium sulfate anion results reported below, are the results for the formate treated solution. These results are reported on both a dry cesium hydroxide basis, and on an equivalent dry cesium sulfate basis to allow direct comparison to the input cesium sulfate results, as were also previously provided above.

| | Input $Cs_2SO_4$ | Formate Treated CsOH | | Calculated $Cs_2SO_4$, Basis CsOH |
|---|---|---|---|---|
| Formate | 8800 ppm | Formate | 460 ppm Formate | 380 ppm |
| Chloride | <100 ppm | Chloride | <100 ppm Chloride | <100 ppm |
| Sulfate | Major Peak | Sulfate | <100 ppm Sulfate | Major |

Example #3

Representative of FIG. 3

Example 3 illustrates the "Two Step" partial conversion process where an input cesium formate salt solution raw material salt is initially converted into a formic acid and formate ion entrained crystallized and purified cesium sulfate product and an impure, excess acidic formate ion, cesium formate mother liquor. However, unlike Example #2, the major excess formate ion (as formic acid and alkali metal formate) treatment processing techniques are deferred until after the primary step of precipitation, crystallization, separation and recovery of the two distinct cesium acid salt streams. Pursuant to this separation, the impure, excess formic acid, cesium formate mother liquor stream is oxidized with hydrogen peroxide until effective completion. The separately recovered alternative purified cesium salt is also subjected to formate ion treatment. Though here, the formate ion is present both as entrained formic acid as well as entrained alkali metal formate.

As previously, analyses are provided in appropriate sections below. Where applicable, references to primary salt component anions like formate, sulfate and/or chloride are reported only as a major or the primary component as detected by Ion Chromatographic analysis (i.e., as applicable, the major or primary anion peak detected).

Added to a 500 ml sample of cesium formate feedstock solution was pure water to a beaker volume of ~680 ml and 83 ml 50% sulfuric acid. To achieve a cesium formate mother liquor density >2.0, this initial reaction solution was boiled down and ambient cooled to a targeted 400-450 ml beaker volume of solution to allow near complete crystallization and precipitation of cesium sulfate crystals from the starting cesium formate solution. When this approximate volume target was achieved, the agitated solution was allowed to cool to room temperature allowing for the near complete crystallization and precipitation of the purified cesium sulfate crystals from the starting cesium formate solution.

It is noted separately, that in stark contrast to Example #2 where hydrogen peroxide was added to fully oxidize the appreciable excess of formic acid present, that here, where no hydrogen peroxide was yet added, there were appreciable formic acid fumes being liberated throughout this thermal processing step.

The purified, though substantively formate ion contaminated, cesium sulfate crystals were then separated from the impure, quite acidic, aqueous cesium formate mother liquor solution by vacuum filtration. Only vacuum drying was applied. The recovered cesium sulfate crystals were then added to pure water and yielded a ~50% cesium sulfate solution. Each of the excess formate ion bearing fractions were separated and recovered. As expected, both were considerably acidic. Both the impure cesium formate filtrate and the purified (ex-formate ion) ~50% cesium sulfate solution were submitted for chemical analysis. The cesium atoms recovered as cesium formate and those recovered as cesium sulfate were calculated. Consistent with the theoretical expectations of the quantity of sulfuric acid added, ~23% of the cesium atoms were recovered as cesium sulfate crystals and ~77% of the cesium atoms were recovered as soluble cesium formate salt. Chemical analyses reported on a dry salt basis for both fractions are provided below. Where applicable, the formate and sulfate content are reported only as a major or the primary component from the Ion Chromatographic analysis (i.e., the major or primary anion peak detected).

| Impure Cs Formate | | Purified $Cs_2SO_4$ | |
| --- | --- | --- | --- |
| Lithium | 1221 ppm | Lithium | 24 ppm |
| Sodium | 2626 ppm | Sodium | 76 ppm |
| Potassium | 1816 ppm | Potassium | 164 ppm |
| Rubidium | 1645 ppm | Rubidium | 1352 ppm |
| Sulfate | 1555 ppm | Sulfate | Major |
| Chloride | 596 ppm | Chloride | <100 ppm |
| Formate | Major | Formate | 51357 ppm |

Added to 305 ml of acidic, impure cesium formate high density brine was 150 ml of each pure water and 35% hydrogen peroxide solution. The combined reaction solution was boiled down to achieve a targeted specific gravity of ~2.15. No formic acid fumes were noted. The resulting solution was then tested for specific gravity, final pH and residual peroxide presence. The measured specific gravity was ~2.1. The previously considerable solution acidity had essentially disappeared with the pH being effectively neutral and measuring at 8-9 and testing for residual peroxide was negative, or undetectable to a sensitivity level of <0.25 ppm. The excess acid formate ion was successfully removed.

No further treatment of the impure cesium formate solution was pursued to remove the very minimal amount of sulfate that was entrained as a cross-contaminant during the vacuum filtration separation of the purified cesium sulfate crystals from the impure soluble cesium formate solution. Traditional well-established sulfate removal techniques, known to those in the art, like barium compound additions, can be pursued, if further sulfate reductions are desired.

Added to ~160 ml of the formate ion laden purified cesium sulfate solution fraction was 320 ml of pure water, 30 ml of hydrogen peroxide and 6 ml of concentrated sulfuric acid. This solution was boiled down to a beaker volume of ~155 ml. No formic acid fumes were detected. To assess the degree of formate ion reduction, the excess sulfuric acid present was first neutralized using hydrated lime and filtered. The ~50% cesium sulfate filtrate sample was tested for formate ion. The dry salt basis formate ion present was reduced from 51357 ppm to 8519 ppm, or ~83% complete. Trace peroxide remained, though only at ~10 mg/liter.

Added to the remaining ~90 ml of sample was an additional 6 ml of hydrogen peroxide solution, 1 ml of concentrated sulfuric acid and 260 ml of pure water. The solution was reacted at 45-85° C., to lessen the degree of peroxide decomposition, for about 8 hours. This solution was then converted from cesium sulfate to cesium hydroxide using barium hydroxide monohydrate. After vacuum filtration separation of the in situ washed barium sulfate gangue from cesium hydroxide, the resulting cesium hydroxide solution was concentrated to ~46% by evaporation and submitted for anion analysis, including formate ion. As in a previous example, the sulfate was purposely removed to alleviate sulfate peak interference to provide a more accurate formate resolution by an Ion Chromatograph instrument. The final anion results, reported on a dry cesium hydroxide basis, are provided below.

| Formate Treated CsOH | |
| --- | --- |
| Formate | <100 ppm |
| Chloride | 133 ppm |
| Sulfate | 142 ppm |

Example #4

CsCl Partially Representative of FIG. 3

Example 4 illustrates the first portion of a "Two Step" partial conversion process where an input cesium formate salt solution raw material is converted into a formic acid and formate ion entrained crystallized and purified cesium chloride product and an impure, excess acidic formate ion, cesium formate mother liquor. However, unlike Example #3, this example is merely intended to illustrate differences one can encounter, like solubility target density, degree of purification, etc., when the intended alternative cesium salt is other than cesium sulfate. The alternative salt, cesium chloride, is used to illustrate.

As with Example #3, if further processing from this initial step were intended, the major excess formate ion (as formic acid and alkali metal formate) treatment processing techniques would be deferred until after the primary step of precipitation, crystallization, separation and recovery of the two distinct cesium acid salt streams. As previously, pursuant to this separation, the impure, excess formic acid, cesium formate mother liquor stream would be oxidized with hydrogen peroxide until acceptable completion. The separately recovered alternative purified cesium salt would also be subjected to formate ion treatment. Though here, the formate ion is present both as entrained formic acid as well as entrained alkali metal formate.

As previously, analyses are provided in appropriate sections below. Where primary salt product applicable, references to primary salt component anions like formate, sulfate and/or chloride are reported only as a major or the primary component as detected by Ion Chromatographic analysis (i.e., as applicable, the major or primary anion peak detected).

Added to a 500 ml sample of cesium formate feedstock solution was 140 ml of ~37% hydrochloric acid. The targeted reaction solution specific gravity was 1.9. If CsCl crystals acted similarly to a saturated CsCl solution, similar to the cesium sulfate based system, it was expected that 286 grams of CsCl crystals would crystallize from the solution and precipitate, basis room temperature. The targeted density was achieved, however, cesium chloride crystals did not form.

Pursuant to this, the solution was evaporated through the application of heat to an aqueous based mother liquor specific gravity of ~2.16, basis room temperature. Densification of the mixed salt solution successfully produced the desired result of forming precipitated cesium chloride crystals. The agitated solution was allowed to cool to room temperature to fully crystallize the cesium chloride crystals from the mixed salt solution.

The purified, though substantively formate ion contaminated, cesium chloride crystals were then separated from the impure, quite acidic, aqueous cesium formate mother liquor solution by vacuum filtration. Only vacuum drying was applied. The recovered cesium chloride crystals were then added to pure water to yield a ~50% cesium chloride solution. Each of the excess formate ion bearing fractions separated and recovered, as expected, were considerably acidic, as determined by pH measurement.

The cesium atoms recovered as cesium formate and those recovered as cesium sulfate were then calculated. If complete cesium chloride precipitation were realized, the theoretical quantity of hydrochloric acid added were ~33% of the cesium atoms being recovered as cesium chloride crystals and ~67% of the cesium atoms being recovered as a soluble cesium formate salt. The actual split realized was 27% recovered as precipitated cesium chloride crystals, 67% recovered as a soluble cesium formate salt and 6% of the cesium atoms remained as soluble cesium chloride salt. A mixed salt solution density higher than the 2.16 achieved is required to realize a separation and recovery more closely approximating the 33%:67% split.

The purified (ex-formate ion), though considerably acidic, ~50% cesium chloride solution, was submitted for chemical analysis. These results are reported in the right side column below. For comparison, chemical analyses of input cesium formate salt solution raw material and this same raw material input adjusted as if reported on a cesium chloride salt basis are also provided. All reported results are on a dry salt basis. Where applicable, the formate and sulfate content are reported only as a major or the primary component from the Ion Chromatographic analysis (i.e., the major or primary anion peak detected).

| Input Formate Sol'n | | Input Adjusted to CsCl Equiv | | Purified CsCl Fraction | |
|---|---|---|---|---|---|
| Lithium | 978 ppm | Lithium | 1034 ppm | Lithium | 137 ppm |
| Sodium | 2511 ppm | Sodium | 2654 ppm | Sodium | 318 ppm |
| Potassium | 1464 ppm | Potassium | 1547 ppm | Potassium | 222 ppm |
| Rubidium | 1583 ppm | Rubidium | 1673 ppm | Rubidium | 407 ppm |
| Sulfate | <100 ppm | Sulfate | <100 ppm | Sulfate | <100 ppm |
| Chloride | 461 ppm | Chloride | Major | Chloride | Major |
| Formate | Major Peak | Formate | NA | Formate | 46859 ppm |

It is also noted that the separated impure cesium formate fraction was analyzed for the degree of cross-contamination of chloride. It was reported to contain 25345 ppm of chloride ion, as reported on a dry cesium formate basis.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of forming an alkali metal salt comprising:
   a) introducing at least one alkali metal formate and at least one acid and reacting the at least one alkali metal formate with the at least one acid to form an alkali metal salt in the presence of formate ions, and
   b) substantially removing said formate ions from said alkali metal salt formed in step a).

2. The method of claim 1, wherein said step of removing comprises adding at least one oxidizer to said alkali metal salt in the presence of formate ions.

3. The method of claim 2, wherein said oxidizer is hydrogen peroxide.

4. The method of claim 1, wherein said removing said formate ions comprises adding at least one base to said alkali metal salt in the presence of formate ions to convert said formate ions to an alkali metal formate salt.

5. The method of claim 4, wherein said base is cesium hydroxide.

6. The method of claim 1, further comprising heating said alkali metal salt during step b) or a part thereof.

7. The method of claim 6, further comprising recovering formic acid vapor overhead produced by said heating of said alkali metal salt as a formic acid.

8. The method of claim 1, wherein oxidizing is utilized to substantially remove said formate ions.

9. The method of claim 1, wherein said removing said formate ions comprises adding heat, at least one oxidizer, base, or any combination thereof to said alkali metal salt.

10. The method of claim 1, wherein said alkali metal formate in step a) is an alkali metal formate solution.

11. The method of claim 10, wherein said alkali metal formate solution is neutralized to a pH of 7 or higher after step b).

12. The method of claim 1, wherein said at least one alkali metal formate is added continuously, semi-continuously, as batches, or increments, or combinations thereof.

13. The method of claim 1, wherein said acid is sulfuric acid.

14. The method of claim 1, wherein said alkali metal salt is cesium sulfate.

15. The method of claim 14, further comprising converting said cesium sulfate or a fraction thereof to cesium hydroxide, cesium carbonate, cesium chloride, or cesium fluoride.

16. The method of claim 1, wherein said alkali metal salt is an alkali metal sulfate.

17. The method of claim 16, further comprising converting said alkali metal sulfate to an alkali metal hydroxide, alkali metal carbonate, alkali metal chloride, or alkali metal fluoride.

18. The method of claim 1, further comprising purifying said alkali metal salt.

19. The method of claim 1, wherein said at least one acid is added continuously, semi-continuously, as batches, or increments, or combinations thereof.

20. The method of claim 1, further comprising filtering the product resulting after step b) to separate any gangue material from said alkali metal salt.

21. The method of claim 1, further comprising crystallizing at least a portion of said alkali metal salt to obtain crystals.

22. The method of claim 21, further comprising re-dissolving said crystals in an aqueous solution.

23. The method of claim 1, wherein substantially removing formate ions is removing at least 50% by weight of said formate ions.

24. The method of claim 1, wherein said step of substantially removing formate ions is removing at least 95% by weight of said formate ions.

25. The method of claim 1, wherein said step of substantially removing formate ions is removing at least 99% by weight of said formate ions.

26. The method of claim 1, wherein said step of substantially removing formate ions is removing at least 99.9% by weight of said formate ions.

27. The method of claim 1, wherein said alkali metal salt in the presence of formate ions is formed by adding said at least one acid in a stoichiometrically deficient amount relative to said at least one alkali metal formate solution.

28. The method of claim 27, wherein said alkali metal salt solution includes a specific gravity sufficient to precipitate a salt of said at least one acid.

29. The method of claim 27, wherein said alkali metal salt solution is evaporated to include a specific gravity sufficient to precipitate a salt of said at least one acid.

30. The method of claim 1, wherein a portion of said alkali metal formate is present with said alkali metal salt after step b).

31. The method of claim 1, wherein said alkali metal formate has a purity and said alkali metal salt has a purity that is greater than said purity of the alkali metal formate.

* * * * *